United States Patent [19]

Lamont

[11] Patent Number: 5,797,862

[45] Date of Patent: Aug. 25, 1998

[54] MEDICAL BOOT FOR PATIENT WITH DIABETIC FOOT

[76] Inventor: William D. Lamont, 54283 Meadowood Ct., Shelby Township, Mich. 48316

[21] Appl. No.: 707,725

[22] Filed: Sep. 4, 1996

Related U.S. Application Data

[63] Continuation-in-part of Ser. No. 521,962, Aug. 31, 1995, and a continuation-in-part of Ser. No. 343,090, Nov. 21, 1994, Pat. No. 5,609,570.

[51] Int. Cl.⁶ .................................................. A61F 5/00
[52] U.S. Cl. .................... 602/10; 602/23; 602/29; 36/43; 36/154; 36/181; 36/93
[58] Field of Search .................. 602/27, 29, 23, 602/65, 9–11; 36/43, 44, 93, 154, 153, 155, 159, 173, 166, 180, 181

[56] References Cited

U.S. PATENT DOCUMENTS

| | | | |
|---|---|---|---|
| 2,088,511 | 7/1937 | Frei | 36/159 |
| 2,613,455 | 10/1952 | Amico | 36/155 |
| 2,794,270 | 6/1957 | Dubner | 36/154 X |
| 3,021,846 | 2/1962 | Scholl | 36/154 |
| 3,641,688 | 2/1972 | Von Den Berken | 36/43 |
| 3,707,784 | 1/1973 | Stafford | 36/11.5 |
| 3,785,070 | 1/1974 | Stafford | 36/44 |
| 3,950,864 | 4/1976 | Cooper et al. | 12/146 D |
| 4,182,055 | 1/1980 | Turner, Jr. | 36/30 R |
| 4,566,197 | 1/1986 | Sitzes | 36/11 |
| 4,603,493 | 8/1986 | Eston | 36/44 |
| 4,627,179 | 12/1986 | McElroy | 36/154 X |
| 4,628,621 | 12/1986 | Brown | 36/44 |
| 4,642,912 | 2/1987 | Wildman et al. | 36/154 X |
| 4,669,142 | 6/1987 | Meyer | 36/154 X |
| 4,706,316 | 11/1987 | Tanzi | 12/142 T |
| 4,747,410 | 5/1988 | Cohen | 36/140 |
| 4,782,605 | 11/1988 | Chapnick | 36/154 X |
| 5,003,708 | 4/1991 | Daley | 36/44 |
| 5,123,180 | 6/1992 | Nannig et al. | 36/93 X |
| 5,184,409 | 2/1993 | Brown | 36/44 |
| 5,216,825 | 6/1993 | Brum | 36/154 X |
| 5,226,245 | 7/1993 | Lamont . | |
| 5,329,705 | 7/1994 | Grim et al. | 36/93 X |
| 5,456,659 | 10/1995 | Gildersleeve et al. | 602/26 X |
| 5,555,584 | 9/1996 | Moore, III et al. | 36/154 |

*Primary Examiner*—Linda C. Dvorak
*Attorney, Agent, or Firm*—Charles W. Chandler

[57] ABSTRACT

A protective boot for patients with arterial disease has an insole formed with a heat activated material to from a permanent impression of the bottom of the patient's foot.

9 Claims, 6 Drawing Sheets

MEDICAL BOOT FOR PATIENT WITH DIABETIC FOOT

CROSS-REFERENCE TO RELATED APPLICATION

This application is a continuation-in-part of U.S. Patent application Ser. No. 08/521,962, filed Aug. 31, 1995 for "Medical Boot With Unitary Splint", still pending; U.S. application Ser. No. 08/343,090, filed Nov. 21, 1994 for "Protective Medical Boot and Orthotic Splint", now U.S. Pat. No. 5,609,570; and also related to Provisional application Ser. No. 60/003,241 filed Sep. 5, 1995 for "Medical Boot for Patient With Diabetic Foot."

BACKGROUND OF THE INVENTION

About twelve percent of the population, that is millions of people, suffer from diabetes. Of this number, many suffer from lower leg and specifically foot complications, such as diabetes mellitus, chronic thrombophlebitis, malnutrition and vitamin deficiency, carcinoma, multiple sclerosis, uremia, vascular disease, and venus stasis ulcers. These conditions, if not treated, and supported properly, can result in the loss of the patient's limb.

SUMMARY OF THE INVENTION

The broad purpose of the present invention is to provide an insole for the medical boot disclosed in my co-pending patent applications as well as my prior U.S. Pat. No. 5,226,245 which issued Jul. 13, 1993. My earlier boots are sold under the trademark T-Boot and Demi-Boot which are respectively a large boot and a smaller boot depending upon the size of the patient.

My novel insole will be provided in three sizes, small, medium and large and two types of laminations. A universal width gives generous room for the diabetic foot. The insole body is a multiple density composite comprising a blue elastic polymer which is unlike foam rubber, which breaks down. The elastic polymer functions are: 1. proper weight distribution; 2. shock and shear absorption and dissipation; 3. posting to accommodate or correct bio-mechanical deficiencies. The polymer, when used as an insole, flows perpendicular to the force of the patient's weight, slowing the velocity prior to impact, then rebounds slowly to reduce after-shock. The material responds to shear force by twisting internally like a liquid ball bearing, so that no shearing action is apparent to the surface.

A pink Plastazolt material is bonded to the blue elastic polymer. Plastazolt is known as a leading material for orthotic appliance fabricators for making custom molded inlays for a number of years. It can be combined with different types of substrate such as foam rubber, which has a tendency to deteriorate in a very short period of time. The Plastazolt permits an impression of the patient's foot. The Plastazolt can be molded to form an impression of the configuration of the bottom of the patient's foot, by heating the surface to a 130° F. for approximately three to four minutes, that is in a relatively short period of time. A patient's own body weight and temperature will also mold the material in the same way during a period of one to two days.

The polymer and the Plastazote are laminated together and combined on top of a thin plastic insole. The two insoles are then disposed in a cover of blue tricot or similar material which has a toe pocket and a heel pocket to hold the two insoles firmly in place. The insole cover has a pair of integral straps that wrap around the bottom of the insoles to assist in connecting the cover to the insole. The assembly is then placed into the bottom of the medical boot disclosed in my prior applications and patent and held in position at the heel portion by hook and loop fabric fasteners. The toe is anchored to the boot by a pair of snap fasteners, or hook and loop fabric fasteners.

The soft laminated insole may also be a combination of a Poron material laminated to the Plastazote material. The Poron material is a frothed, open cell urethane sheet that is breathable, comfortable, odorless, washable and non-sensitizing. It absorbs shock, cushions and will recoil without bottoming out.

For greater customization, a metatarsal pad made of the same elastic polymer is attached by an adhesive that is located according to reference markings on the blue polymer insole. The pad lifts a portion of the patient's sole and reduces pressure to the metatarsal heads, thus reducing skin breakdown and ulcer formation. Ulcer formation in the diabetic patient can lead to infection and possible amputation if not treated and supported in very early stages. Scaphoid pads are of the same elastic polymer material but are generally wedge-shaped and attached by an adhesive applied to the bottom of the polymer insole. These pads provide greater cradle support to the arch of the patient's foot, and provide a significant anatomical fit which also reduces pressure and tissue breakdown. The metatarsal pads and scaphoid pads can be used as wedges for the hind foot, fore foot, or both, in the middle or the side. The wedges transfer weight while standing or during ambulation, to the opposite side of the foot for added support, stabilization, equalized weight distribution or balance.

A combination of the diabetic insole together with the soft upper boot of my medical boot protects both the lower leg and foot. It provides drastic cost savings over custom made leather shoes and custom molded inserts.

The polymer insoles can be trimmed and placed into a regular street shoe or athletic shoe when the insole of the street shoe or athletic shoe is removed creating a ¼" recess.

The polymer insole, when utilized with my soft medical boot, offers even greater advantages for splinting the foot, ankle or leg to offer more support. The splint integrates into the boot while accommodating the insole. Thus, my product provides three appliances in one:

1. wound care protection (body of boot material);
2. bracing for the lower leg and foot with an integrated splint;
3. custom fitted, hi-tech polymer insole for support and pressure reduction to the plantar surface of the foot.

When these three items are combined, my product becomes a multi-porous splint brace with a customized polymer insole. Other multi-porous splints are available, but do not offer a multiple inlay for ambulation.

A further object is to provide an improved hydro-cushion pillow over that disclosed in my U.S. Pat. No. 5,226,245.

The improved cushion now extends to the calf area to protect the leg for pressure or abrasion from the splint. The gel in the cushion protects the patient's heel in bed, walking or sitting in a wheelchair, cushioning and absorbing pressure. The cushion has a zipper to permit the gel to be removed during ambulation, to reduce the weight of the boot, but still giving padding to the lower calf and wings of the cushion. This in turn gives greater stability to the internal and external ankle portion of the foot. The zipper also permits the gel to be removed for washing and drying of the cushion cover.

In order to further fasten the boot to the patient's foot, the boot sole has slots which accommodate a strap that is fed through the slots and then wrapped around the boot and the foot. The strap ends are connected by hook fabric fasteners to the boot material to compress the boot against the foot, holding the foot stable and eliminating constriction directly against the foot.

An upper strap wraps around the patient's ankle and the ankle portion of the boot. The upright portion of the splint has slots for recovering the mid-section of the upper strap. This strap is identical to the foot strap, with hook fabric fasteners that can be connected either to the boot material or the strap end.

The splint is connected to the boot by a snap fastener at the top of the splint, and a pair of snap fasteners that connected the inside toe cover to the toe of the boot. A cap at the top of the splint prevents abrasion of the calf area.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which.

DESCRIPTION OF THE PREFERRED EMBODIMENT

Figure 1:
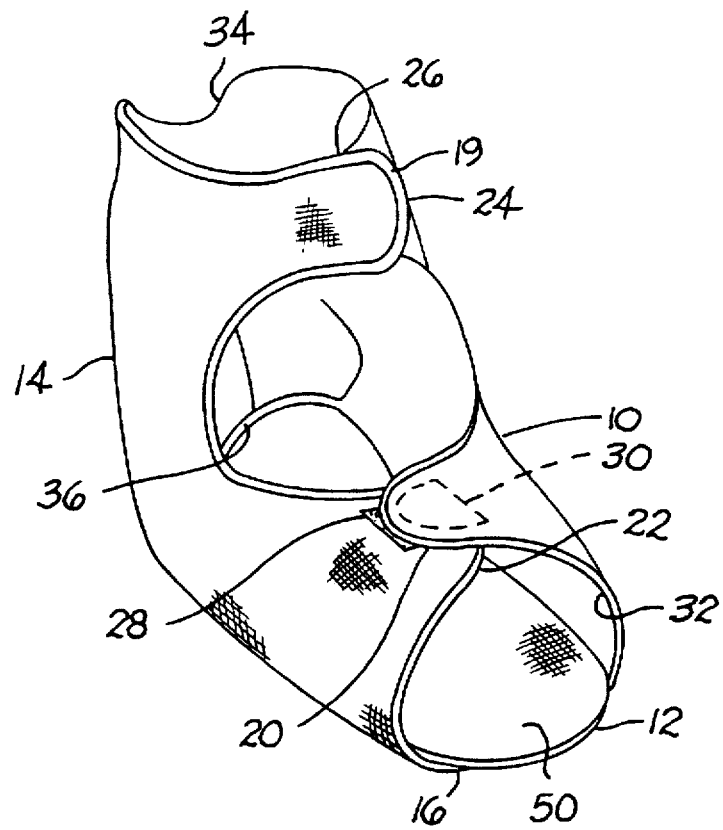
FIG. 1 is a perspective view of a soft medical boot with a diabetic insole illustrating the preferred embodiment of the invention.

Referring to the drawings, FIG. 1 illustrates a soft medical boot 10 showing a preferred diabetic insole 12. Boot 10 has a height of about 10" and a length from heel to toe about 10".

The boot has an upper leg portion 14 and a sole 16. The boot is formed of a single multi-layer sheet containing the profile of the leg portion in the sole. The sole is formed from a pair of edges that are stitched together to form a seam 18 extending from the heel to the toe of the boot.

The boot material is made of an elastomeric shape-retaining material, such as a soft, flexible, compressible, open cell polyurethane foam core with an outer layer of an ultra-smooth, soft, non-allogenic cloth such as brushed tricot. This fabric is characterized by a continuous layer of small loops which make the material compatible with fabric hook fasteners means such as Velcro fasteners. The entire outer cover, including both the upper portion of the boot and the sole has a brushed tricot covering so that a patch of a Velcro type hook material can be connected at any location on the boot exterior.

The entire edge of the boot above the sole is heat fused and compressed together as at 19 and cut to the boot configuration all in one process.

Figure 2:
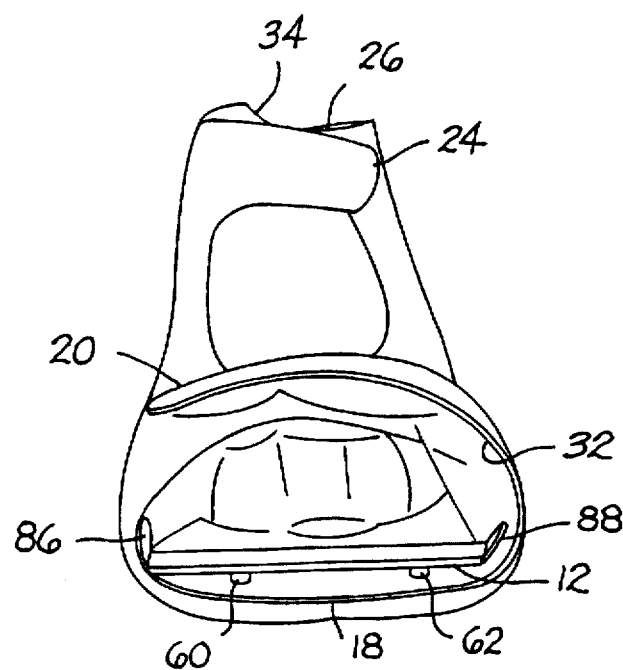
FIG. 2 is a view of the boot and insole of FIG. 1 when viewed through the open toe.

The boot has a pair of cooperating foot straps 20 and 22, and a pair of cooperating leg straps 24 and 26. Foot strap 22 has a patch 28 of a fabric hook material which may be connected to a complementary patch 30 of a fabric loop material on strap 20 to close the boot around a patient's foot to form a relatively large toe opening 32. Similarly the leg straps have cooperating patches of fabric hook and loop fastener material to close the boot to the position illustrated in FIGS. 1 and 2, such that the boot encircles the user's lower calf.

The top rear of the boot has a recessed area at 34 which extends down about 1½" from the top of the boot, and is about 3½" wide to protect the rear of the user's leg against skin irritation and to prevent constriction of capillary flow in the lower calf area of the leg.

Referring to FIG. 1, the boot heel has an opening 36 that is about 2¾" wide from side to side and is about ¼" tall for receiving a splint, not shown, but disclosed in my co-pending patent application, and to provide greater air circulation in the heel area.

Figure 3:
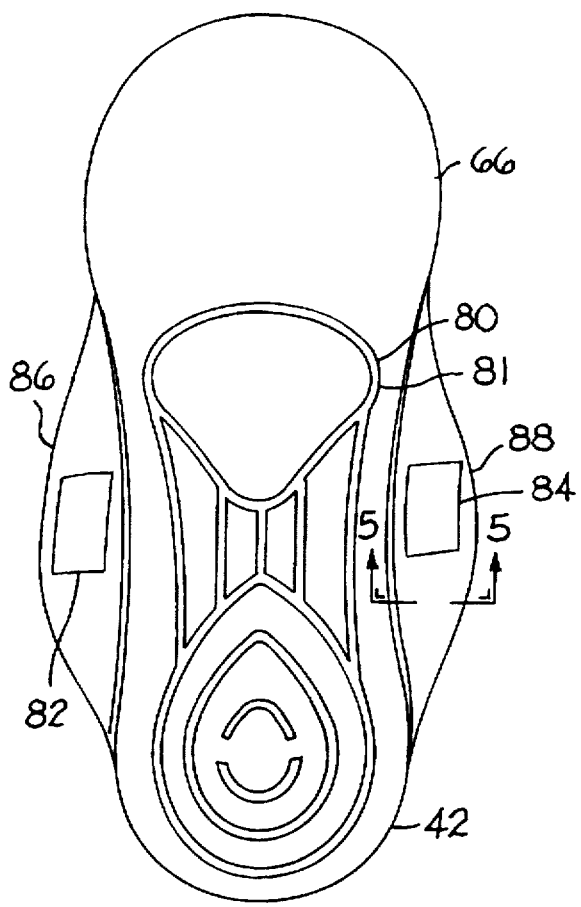
FIG. 3 is a view of the bottom of the polymer insole.
Figure 9:
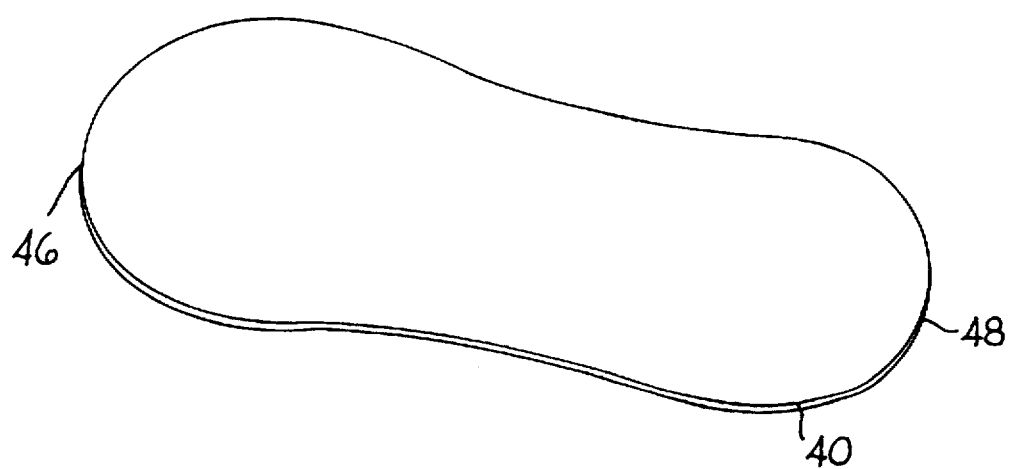
FIG. 9 is a view of the relatively rigid plastic insole.
Figure 10:
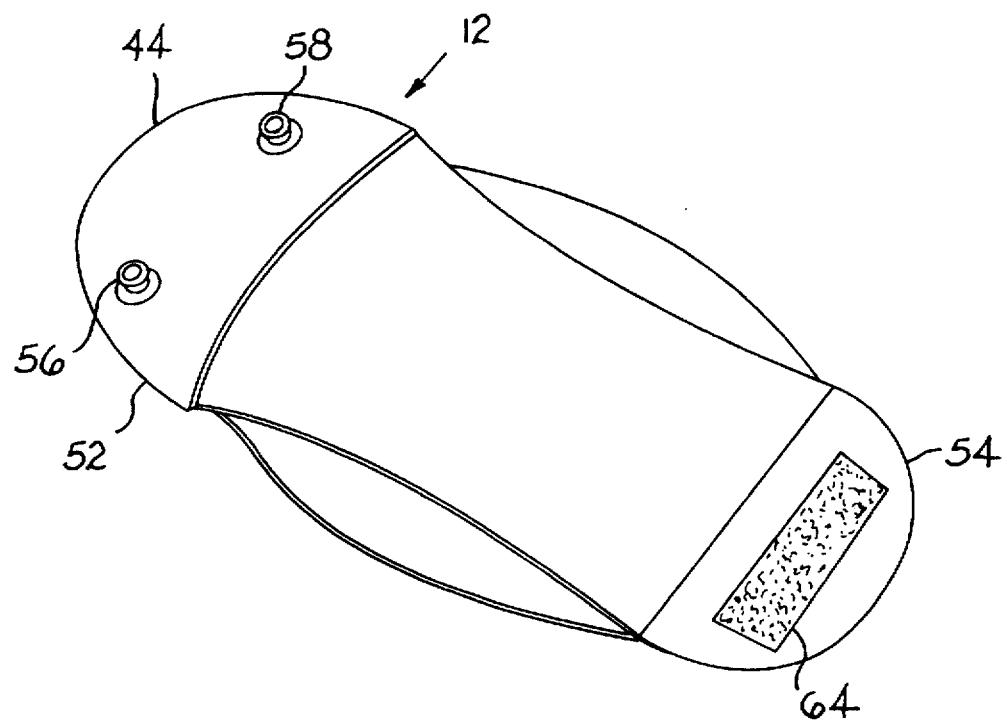
FIG. 10 illustrates the heel and toe covers for the preferred insole.

Referring to FIGS. 3, 9 and 10, diabetic insole assembly 12 comprises a hard insole 40, a plastic insole 42, and a cover 44 which holds the two insoles together as a unit.

FIG. 10 shows the liner and the insoles in the upside down position. Hard insole 40 is elongated with a toe end 46 and a heel end 48. The hard insole is available in various lengths, such as small, medium and large for a typical boot. The hard insole and cover 44 extend beyond the toe opening of the boot so that the patient's toes are well ventilated. Hard insole 40 is formed of a relatively rigid polypropylene plastic material and is about ¼" thick, and for illustrative purposes may be 9½" long. The hard insole provides some foundation support for the patient when he is either walking with the boot or confined to bed.

Insole cover 44 has a top layer 50, as seen in FIG. 1, formed with a soft foam interior and a brushed tricot upper surface to provide a soft surface contacting the sole of the patient's foot. Referring to FIG. 10, the bottom side of the cover has a pair of pockets 52 and 54 for receiving the heel and toe respectively of the two insoles.

Pocket 52 has a pair of male snap fasteners 56 and 58 which mate with a pair of female snap fasteners fastened to the bottom of the boot. The snap fasteners locate the insoles and prevent them from slipping in the boot as the patient is either walking or lying in a supine position. A patch of a Velcro hook-shaped fabric fastener means 64 is attached to the bottom of heel pocket 54 for connecting the liner either to the heel portion of the boot or to the foot portion of a splint (now shown).

Figure 5:
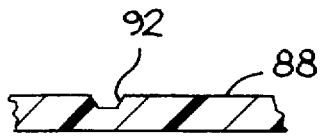
FIG. 5 is an enlarged cross-section as seen along lines 5—5 of FIG. 3.
Figure 4:
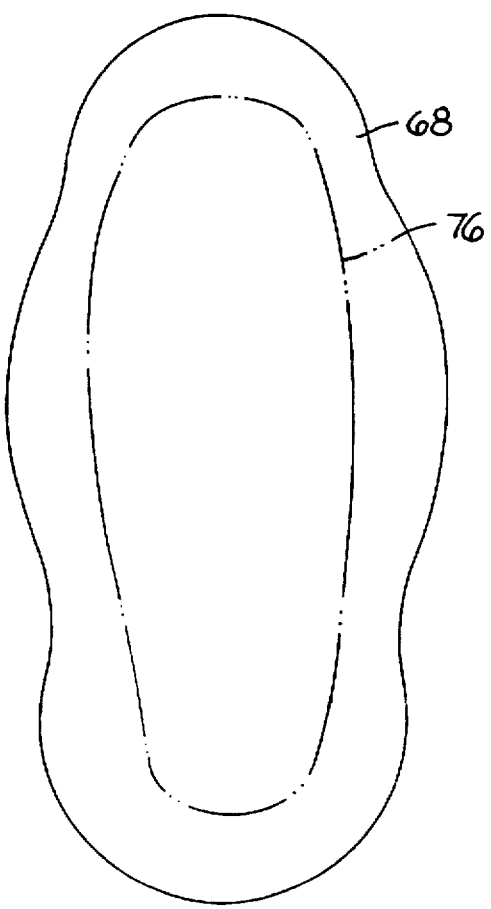
FIG. 4 is a view of the Plastazote insole with an image of the patient's foot illustrated in phantom.
Figure 6:
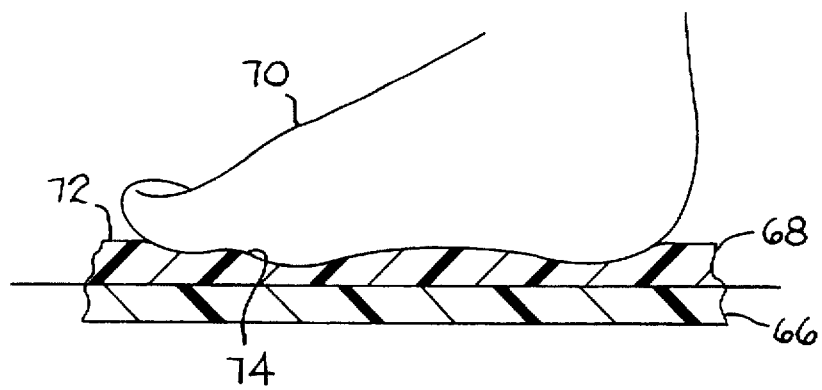
FIG. 6 is a view of a patient forming an impression of his foot in the Plastazote side of the insole.

Referring to FIGS. 3 to 8, insole 42 is a multiple density composite comprising a blue lower polymer layer 66 and a pink Plastazote top layer 68 bonded to layer 66. Plastazote is a material used for forming the impression of a patient's foot 70 as illustrated in FIG. 6. The surface 72 of the Plastazote is heated to approximately 130° for three to four minutes, as by a hair dryer or the like. The patient's foot is then placed on the Plastazote to form a recessed impression 74. When he removes his foot, impression 74 forms a permanent recessed area in the Plastazote. The impression is illustrated generally in FIGS. 6 and 7, and at 76 in phantom in FIG. 4.

Figure 7:
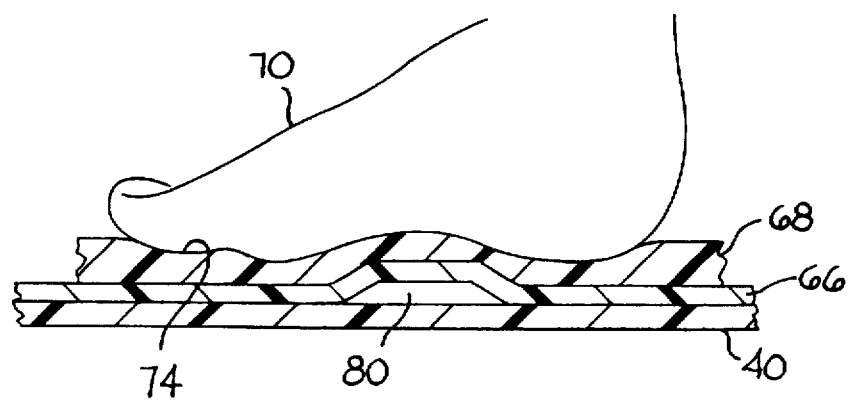
FIG. 7 shows the manner in which the metatarsal pad elevates the mid-section of the patient's foot to relieve the pressure to the metatarsal heads.
Figure 8:
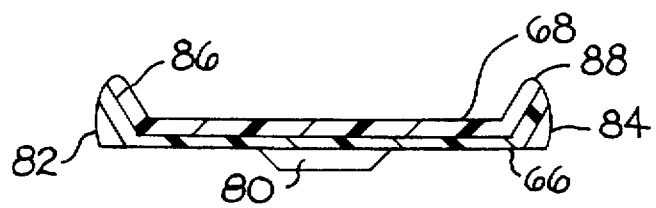
FIG. 8 is a view generally at right angles to the views of FIG. 7 to show the location of the metatarsal pad and wedges.

Referring to FIGS. 3, 7 and 8, a metatarsal pad 80 made of the same elastic polymer as layer 66 is attached to the bottom of layer 66 and located according to reference marking 81. Pad 80 when placed on hard insole 40 lifts the bottom of the patient's foot as illustrated in FIG. 7, thereby reducing pressure to the metatarsal heads and reducing the possibility of skin breakdown and ulcer formation.

Referring to FIG. 8, a pair of wedge-shaped scaphoid pads 82 and 84 can also be attached by a suitable adhesive, to the flanged or winged areas 86 and 88 of polymer layer 66. Flanged areas 86 and 88 swing away from the plane of the layer by virtue of small groove means 90 as illustrated in FIG. 5 which permit the two flanged areas to swing up to the positions illustrated in FIG. 8. This permits the soft insole to provide lateral support to the patient's foot when it is disposed inside the soft boot, illustrated in FIG. 2.

Figure 11:
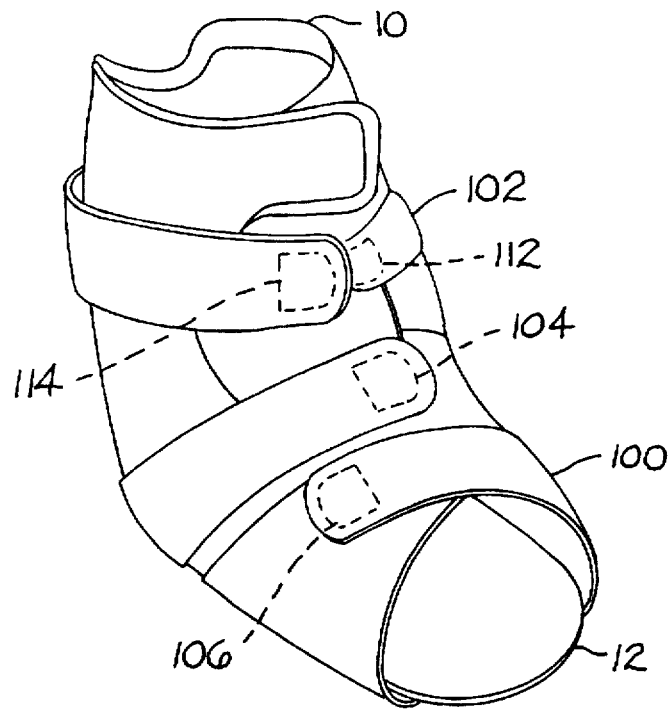
FIG. 11 is a view of another embodiment of the invention which includes two additional straps.
Figure 12:
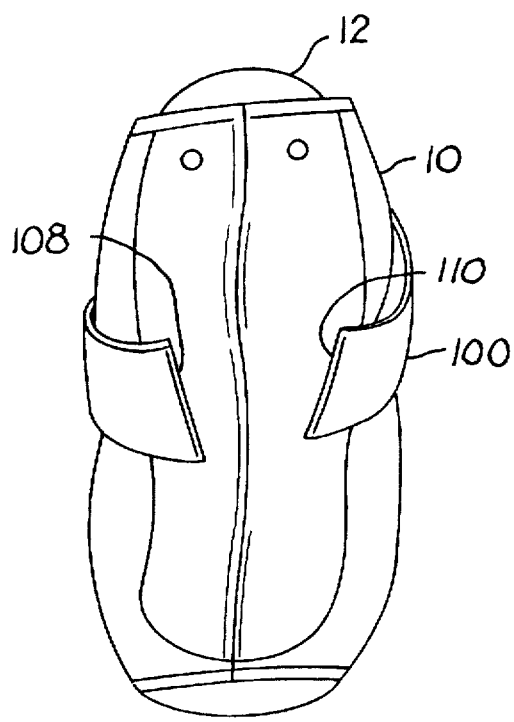
FIG. 12 is a bottom view of the foot portion of the embodiment of FIG. 11.
Figure 13:
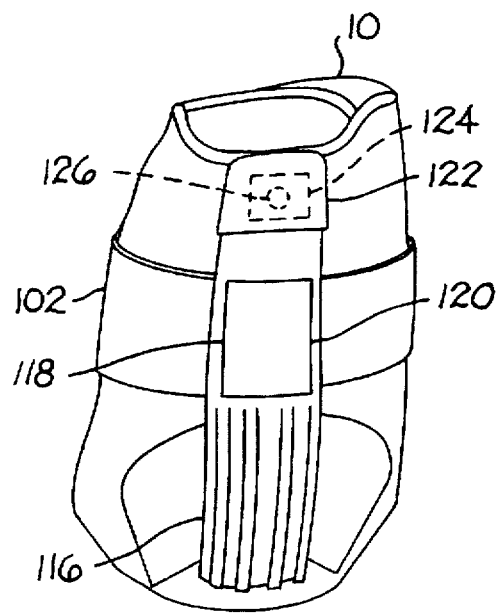
FIG. 13 is a rear view of the calf portion of the embodiment of FIG. 11.

FIGS. 11, 12 and 13 illustrate another embodiment of the invention in which boot 10 has an additional strap 100 encircling the foot portion of the boot, and another strap 102 encircling the calf portion of the boot. Strap 100 and 102 are each about 21" long and 2¼" wide. The strap is formed with an outer layer that is the same as the outer layer of the boot, that is an ultra-smooth, soft, non-allergenic cloth such as brushed tricot. The outer layer has a continuous layer of small loops that makes the material compatible with fabric hook fasteners. The inner layer, that is the layer facing the boot, is preferably formed of a soft wicking material. Strap 100 preferably has a patch of a fabric fastener hook material as illustrated at 104 adjacent one end of the strap and a second patch of a fabric fastener hook material 106 adjacent the opposite end of the strap. Thus the strap can be wrapped around the foot portion of the boot and the ends attached either to the outer layer of the opposite end of the strap, or to the boot material itself.

Referring to FIG. 12, the sole of the boot has a pair of slots 108 and 110 for receiving the midsection of strap 100. The outer ends of the strap are attached to the boot as illustrated in FIG. 11.

Similarly, strap 102 is identical to strap 104 and has a pair of fabric hook fastener patches 112 and 114 attached to the inner layer of the strap adjacent its ends so that they can be fastened to one another as illustrated in FIGS. 11.

Referring to FIG. 13, when the boot is used with a splint 116 having an upright section that extends up the rear calf of the user, the splint has a pair of slots 118 and 120 for receiving the midsection of strap 102 and locating it in position. The strap can be used directly on the boot when the splint is not being used.

A cloth cap 122 mounted on the upper end of the splint has a patch 124 of a fabric hook fastener attached to the boot cover. In addition, snap fastener means 126 carried on the splint and the boot also attach the splint to the boot.

Figure 14:
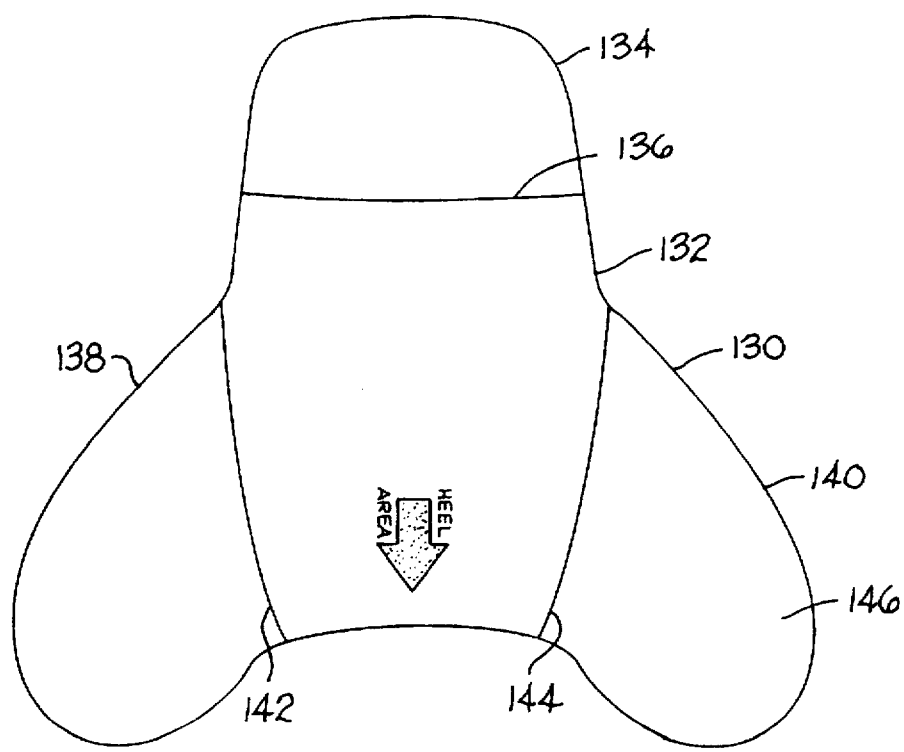
FIG. 14 is a view of a cushion that may be folded and used in the internal heel portion of the embodiment of FIG. 11.

FIGS. 13 and 14 illustrate a cushion 130 which may be folded and used inside the boot adjacent the rear opening in the manner described in my prior U.S. Pat. No. 5,226,245 which issued Jul. 13, 1993 for "Protective Boot Structure". The cushion may be used under the heel cord of the patient. The cushion is formed in a unitary structure. The cushion has a central somewhat rectangular midsection panel 132 connected to a top smaller rectangular panel 134 along a stitched fold line 136. The cushion also has a pair of side panels 138 and 140 connected along stitched fold lines 142 and 144 respectfully.

The midsection panel, the top panel and the side panels all house an elastomeric shape-retaining material such as a soft flexible compressible open core polyurethane foam or the like. The side of the cushion facing the patient's foot, including all four panels, is formed with a covering at 146 of a soft material having good wicking characteristics as is the opposite side of the two side panels. The side illustrated in FIG. 5, which faces the inner surface of the boot, including top panel 134 and midsection 132 are formed with the same material as the outer covering of the boot body, that is a non-allergenic brushed tricot having a continuous layer of small loops compatible with Velcro hook fasteners.

Figure 15:
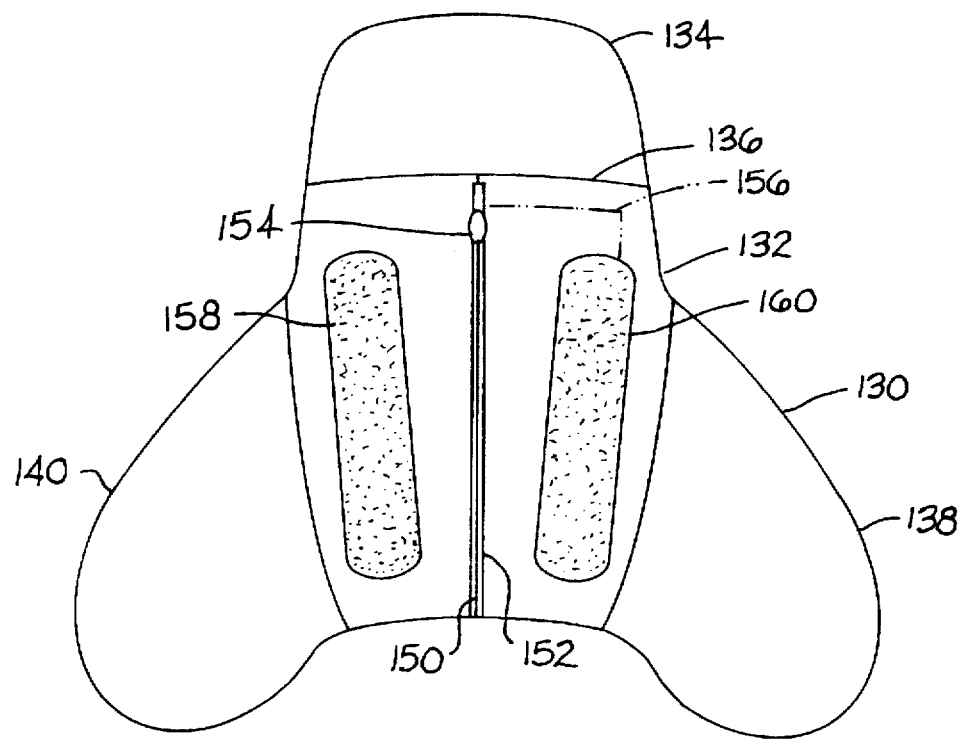
FIG. 15 is a view of the opposite side of the view of FIG. 14 to show the zipper closure.

Midsection 132, illustrated in FIG. 15 has a central opening at 150 running the full height of section 132, fastened to a zipper closure 152 which provides access to the interior of the panel. A zipper handle 154 is employed by the user for zipping or unzipping the closure. In FIG. 15 the zipper is illustrated as being in the fully closed position.

The interior of the panel houses a fluid-containing pouch generally indicated in phantom at 156 which entirely fills the interior of the panel. The zipper permits pouch 156 to be removed so that the cushion cover can be cleaned. Pouch 156 is a fluid containing pouch of the type described and shown in FIGS. 4, 6 and 7 U.S. Pat. No. 5,226,245, incorporated herein by reference. Strips of fabric hook-shaped fasteners and matable with the boot cover 158 and 160 are attached to the midsection panel, parallel to the zipper closure. Preferably the strips are each about 1" in width and about 4" in length in order to connect the pouch in a selected location to the interior of the boot.

Having described my invention, I claim:

1. An insole adapted for removable placement in a medical boot, wherein the boot comprises a compressible foam material designed to at least partially enclose a person's foot, said insole comprising:

an upper layer adapted to engage the undersurface of a person's foot when the foot is positioned in a medical boot, said upper layer being formed of a heat-activated moldable plastic material adapted to conform to the surface contour on the undersurface of a person's foot and to form a permanent impression thereof;

a lower polymer layer bonded to said upper layer, said lower layer being formed of an elastic resilient material having the ability to flow perpendicular to the direction of an applied force, whereby the polymer layer provides a shock absorption capability to the insole;

said upper and lower layers being bonded together to form a multiply flexible laminate having a front toe area, a rear heel area, and an intermediate metatarsal area;

a resilient elastic pad bonded to the undersurface of said lower polymer layer, whereby a portion of the person's foot is elevated according to the thickness of the pad; and a relatively hard bottom layer (40) attached to said elastic pad and said lower polymer layer to form a bottom surface of the insole, said hard bottom layer being formed of a relatively rigid, non-yielding flexible material resistant to deformation forces, whereby said bottom layer provides a foundational support for a person's foot.

2. The insole of claim 1, wherein said bottom layer has a thickness of about ¼".

3. The insole of claim 1, and further comprising two wing sections extending from metatarsal areas of said polymer layer to extend upwardly from the major plane of the insole, to provide lateral support for the persons's foot.

4. The insole of claim 3, wherein said polymer layer and said wing sections are formed of a single polymer sheet.

5. The insole of claim 4, wherein said polymer layer and said wing sections have hinge connections defined by grooves formed in the upper surface of the polymer sheet.

6. The insole of claim 1, and further comprising a cover spanning the upper surface of said upper layer, a first pocket-forming fabric (52) attached to said cover to encircle the toe area of said multi-ply laminate, and a second pocket-forming fabric (54) attached to said cover to encircle the heel area of said laminate, whereby the cover is removably retained on the laminate.

7. The insole of claim 6, wherein said cover is formed of a soft foam material having a brushed tricot outer covering.

8. The insole of claim 1, wherein said lower polymer and said elastic pad are formed of the same polymer material.

9. A medical boot comprising:

a two piece boot body that comprises a soft flexible upper panel, and a soft flexible lower panel joined together to form a protective boot around the wearer's foot and lower leg;

said lower panel including a peripheral edge defining the sole of the boot body;

said upper panel having an integral leg strap adapted to extend across the front surface of the wearer's leg, and an integral foot strap adapted to extend across the upper surface of the wearer's foot;

an insole adapted for placement under a person's foot disposed in said boot body to provide a cushioned foundational support, said insole comprising;

an upper layer adapted to engage the undersurface of a person's foot, said upper layer being formed of a heat-activated moldable plastic material adapted to conform to the surface contour on the undersurface of a person's foot and to form a permanent impression thereof;

a lower polymer layer bonded to said upper layer, said lower layer being formed of an elastic resilient material having the ability to flow elastically perpendicular to the direction of an applied force, whereby the polymer layer provides a shock absorption capability to the insole; and a relatively hard bottom layer disposed in the boot body between the lower polymer layer and the sole of the boot body and spanning the entire area of said lower polymer layer, said bottom layer being formed of a non-yielding flexible material resistant to deformation forces, whereby the bottom layer provides foundational support for a person's foot.

* * * * *